US010733266B2

(12) United States Patent
Whitehurst

(10) Patent No.: US 10,733,266 B2
(45) Date of Patent: Aug. 4, 2020

(54) SYSTEMS AND METHODS OF PROVIDING PATIENT APPS

(71) Applicant: Apple Inc., Cupertino, CA (US)

(72) Inventor: Todd K. Whitehurst, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 848 days.

(21) Appl. No.: 15/014,856

(22) Filed: Feb. 3, 2016

(65) Prior Publication Data

US 2017/0011182 A1 Jan. 12, 2017

Related U.S. Application Data

(60) Provisional application No. 62/189,480, filed on Jul. 7, 2015.

(51) Int. Cl.
*G06F 19/00* (2018.01)
*G16H 80/00* (2018.01)
*G16H 50/20* (2018.01)

(52) U.S. Cl.
CPC .......... *G06F 19/328* (2013.01); *G06F 19/325* (2013.01); *G16H 50/20* (2018.01); *G16H 80/00* (2018.01)

(58) Field of Classification Search
CPC ........ G16H 40/63; G16H 40/67; G16H 10/65; G16H 40/40
See application file for complete search history.

(56) References Cited

U.S. PATENT DOCUMENTS 6,820,057 B1 11/2004 Loch et al.
8,005,691 B2 8/2011 Kumar et al.
(Continued)

FOREIGN PATENT DOCUMENTS

CN 101393520 A 3/2009
CN 101667224 A 3/2010
(Continued)

OTHER PUBLICATIONS

"Non-Final Office Action", U.S. Appl. No. 15/019,730, dated Jul. 2, 2018, 15 pages.
(Continued)

*Primary Examiner* — Reginald R Reyes
(74) *Attorney, Agent, or Firm* — Kilpatrick Townsend and Stockton LLP

(57) ABSTRACT

Methods of selection of health related applications and treatment and diagnosis using health related applications are provided herein. Methods include selection of a first set of health related apps by a physician for use in treatment or diagnosis of a health condition, selection of an app from the first set by the patient with a first portable device. In one aspect, the applications are provided and managed by a service providers and include regulated health related apps. In some methods, the system communications with an insurer so as to indicate to a patient an insurance related attribute associated with each app to facilitate selection by the patient. In another aspect, methods include communication of health data elements obtained with the first portable device to the health service provider for tracking or analysis and subsequent communication between any of the first portable device and the service provider, insurer and physician.

21 Claims, 9 Drawing Sheets

(56) References Cited

U.S. PATENT DOCUMENTS

| | | | |
|---|---|---|---|
| 8,157,730 B2 | 4/2012 | Leboeuf et al. | |
| 8,423,387 B1 | 4/2013 | Mirza | |
| 8,715,181 B2 | 5/2014 | Brynelsen et al. | |
| 8,737,971 B2 | 5/2014 | van Rooyen et al. | |
| 8,818,823 B2 | 8/2014 | Ackerson et al. | |
| 8,930,221 B2 | 1/2015 | Patterson et al. | |
| 9,014,779 B2 | 4/2015 | Hutchison et al. | |
| 9,582,642 B2 | 2/2017 | Keen et al. | |
| 2001/0032100 A1 | 10/2001 | Mahmud et al. | |
| 2001/0037219 A1 | 11/2001 | Malik et al. | |
| 2002/0005935 A1 | 1/2002 | Robin | |
| 2003/0028400 A1 | 2/2003 | Christ et al. | |
| 2003/0074221 A1 | 4/2003 | Christ et al. | |
| 2004/0054760 A1 | 3/2004 | Ewing et al. | |
| 2004/0162466 A1 | 8/2004 | Quy et al. | |
| 2005/0049898 A1 | 3/2005 | Hirakawa | |
| 2006/0064030 A1* | 3/2006 | Cosentino | A61B 5/0031 600/547 |
| 2006/0248593 A1 | 11/2006 | Dennis et al. | |
| 2006/0277076 A1 | 12/2006 | Hasan et al. | |
| 2007/0299316 A1 | 12/2007 | Haslehurst et al. | |
| 2008/0120707 A1 | 5/2008 | Ramia | |
| 2011/0295616 A1* | 12/2011 | Vesto | G06F 3/0486 705/3 |
| 2012/0101847 A1* | 4/2012 | Johnson | G06Q 10/00 705/3 |
| 2012/0313776 A1 | 12/2012 | Utter et al. | |
| 2013/0030836 A1 | 1/2013 | Ackerson et al. | |
| 2013/0064358 A1 | 3/2013 | Nusbaum | |
| 2013/0197942 A1 | 8/2013 | Chiu et al. | |
| 2013/0275151 A1 | 10/2013 | Moore et al. | |
| 2013/0304511 A1 | 11/2013 | Gunter | |
| 2014/0081662 A1 | 3/2014 | Bradrick et al. | |
| 2014/0122125 A1 | 5/2014 | Deshpande et al. | |
| 2014/0135592 A1 | 5/2014 | Ohnemus et al. | |
| 2014/0242698 A1 | 8/2014 | Smith et al. | |
| 2014/0257851 A1 | 9/2014 | Walker et al. | |
| 2014/0276552 A1 | 9/2014 | Nguyen et al. | |
| 2014/0278474 A1 | 9/2014 | McClure et al. | |
| 2015/0242592 A1* | 8/2015 | Weiss | G06F 19/3456 705/2 |
| 2015/0244852 A1* | 8/2015 | Erickson | G01N 21/31 455/557 |
| 2015/0294090 A1 | 10/2015 | Kodiyan et al. | |
| 2015/0347499 A1 | 12/2015 | Keen et al. | |
| 2015/0347684 A1 | 12/2015 | Keen et al. | |
| 2015/0347690 A1 | 12/2015 | Keen et al. | |
| 2015/0347784 A1 | 12/2015 | Daniel | |
| 2016/0210416 A1 | 7/2016 | Whitehurst | |
| 2016/0267238 A1 | 9/2016 | Nag | |
| 2016/0301792 A1* | 10/2016 | Lee | A61B 5/6898 |

FOREIGN PATENT DOCUMENTS

| | | |
|---|---|---|
| CN | 103182175 A | 7/2013 |
| WO | 2015/183495 | 12/2015 |

OTHER PUBLICATIONS

"Office Action", China Patent Application No. 201580028726.9, dated Jul. 31, 2017, 15 pages.

"Non-Final Office Action", U.S. Appl. No. 14/998,287, dated Nov. 7, 2018, 29 pages.

* cited by examiner

|  | 502 | 504 | 506 | 508 | 510 | 510 |
|---|---|---|---|---|---|---|
|  | APP | App Service Provider | CO-PAY | REIMBURSEABLE? | Network | Incentive |
| 512 | Heart Rate | Health Inc. | $0 | YES | N/A | N/A |
| 514 | Heart Tracker | Stanford | $10 | YES | in-network | N/A |
| 516 | Heart Monitor | Cedars-Sinai | $15 | YES | in-network | N/A |
| 518 | BP Tracker | Mobile Health, Inc. | $15 | NO | Out-of-network | N/A |
| 520 | Heart Health | Heart Inc. | $25 | NO | Out-of-network | $5/month |

FIG. 5

SYSTEMS AND METHODS OF PROVIDING PATIENT APPS

CROSS REFERENCES TO RELATED APPLICATIONS

The present application claims the benefit under 35 USC §119(e) of U.S. Provisional Appln. No. 62/189,480 filed Jul. 7, 2015; the full disclosure which is incorporated herein by reference in its entirety for all purposes.

The present application is related to U.S. 62/096,091 filed Dec. 23, 2014, entitled "Improved Methods of Treatment and Diagnosis Using Enhanced Patient-Physician Communication;" U.S. 62/129,691 filed Mar. 6, 2015, entitled "Systems and Methods for Facilitating Health Research;" and U.S. 62/005,919 filed May 30, 2014, entitled "Managing User Information—Source Prioritization;" the entire contents of each are hereby incorporated by reference for all purposes.

FIELD OF INVENTION

The present invention relates to identification and selection of health related applications ("apps") with a portable computing device by a patient that are prescribed by a physician for use in methods of treatments and diagnosis of the patient.

BACKGROUND OF THE INVENTION

Medical treatments and diagnostics in the modern healthcare system often involve tracking and analysis of a multitude of patient information and medical records to various health care providers for each patient. Current health care systems can be complex and fragmented resulting in redundancies and inefficiencies in collecting data that frustrate both patient and physician and delay diagnosis and treatment. Although the development of electronic medical records has improved tracking and analysis of health information somewhat, in recent years, acquisition of health information and various health metrics outside of the electronic medical records has increased dramatically. The usefulness of such health information, however, is limited given the complexities and burden associated with dissemination of such large amounts of information. In particular, while there have been huge advancements in technologies that could make it easier for patients to interact with their own medical data, software that manipulates the most important data have been selected and prescribed entirely by physicians, rather than allowing the patients themselves to choose the interface applications that would work best for themselves. In addition, current treatment and diagnostic methods typically limit the quantity and quality of interaction with the patient beyond in-person visits with the physician, which can limit the effectiveness of treatment and reduce patient compliance.

BRIEF SUMMARY OF THE INVENTION

Methods of the present invention pertain to prescribed health related applications for use on a portable computing device of a patient that utilize a patient's personal health data to provide improved treatment and diagnosis of the patient. In particular, methods and system pertain to facilitating selection of health related applications by a physician and selection of one or more of the applications by the patient for use on a portable computing device of the patient. By facilitating identification of a group of health related applications or apps by a physician for use in treatment or diagnosis and selection of the identified application by the patient, and by allowing the patient to choose which of those identified applications would be most appropriate for that patient to interact with, the methods and system of the invention facilitates use of more specialized applications that allows more flexibility for the patient, thereby providing a more personalized treatment and improved patient compliance. In one aspect, such methods allow the physician to prescribe select applications to a patient as needed for a particular treatment or diagnosis. Typically, the apps selected are developed and maintained by a third-party health service provider for use on a portable computing device. Such methods may utilize a first-party framework on the portable computing device of the patient that facilitates identification of a set of prescribed apps in response to a physician input and displays the set of applications on the portable computing device for selection by the patient. In some embodiments, the display further include additional attributes associated with the identified applications to inform the patient's selection. These attributes may include a description or summary of the app, insurance information (e.g. coverage, co-pay, reimbursement, benefits, incentives), or various other aspects of the identified applications.

In some embodiments, methods of treating a patient include identifying a first set of applications relating to a treatment of the patient in response to a physician input, each application of the set being configured for operation on a first portable computing device of the patient and displaying on a graphical user interface of the first portable computing device one or more indicators of one or more applications of the first set. In some embodiments, the first set of applications includes a set of alternatively selectable prescribed applications identified using the physician computing system in response to a physician prescribing any of the first set of applications, and the method include receiving, with the first portable computing device of the patient, data identifying the first set of applications from the physician computing system.

The patient then selects one or more health related applications from the one or more indicators displayed on the graphical user interface in response to an input received with the first portable computing device, after which the one or more selected applications are installed on the first portable computing device. The system then initiates communication of a plurality of health data elements accessed by the device to a medical service provider associated with the selected application. In some embodiments, the one or more applications are a subset of the set of applications identified based on an attribute of the patient, which may include a demographic or status of the patient and the like.

In some embodiments, once the selected health related applications are installed on the portable computing device of the patient, the system outputs health data to the medical service provider associated with the health application, the physician and/or the insurer or health care provider. The health data elements may include any of: a user input entered by the user on the graphical user interface of the first portable computing device, an output of one or more sensors associated with the first portable computing device, an electronic medical record maintained by the physician, data received from an output of one or more sensors associated with the first portable computing device, or any combination thereof. The one or more sensor devices may be FDA regulated devices and may detect any of: activity level, activity tracking, respiration, body temperature, heart wellness data, hydration levels, perspiration, blood glucose, salinity, sleep cycles, posture, $O_2$ levels, muscle engagement, or any combination thereof. Examples of such devices include a cardiac sensor and/or an activity level sensor for treatment of a cardiac condition, an $O_2$ level sensor for treatment of chronic lung disease, a blood glucose meter for treatment of diabetes. The system may be configured such that receiving the input comprises automatically receiving sensor data from one or more sensor devices over a duration of time. In some embodiments, the first portable computing device comprises a first-party application framework through which the one or more applications are displayed to the patient and selected with the first portable computing device.

In another aspect, methods of treating and/or diagnosing a patient include: identifying, in response to a physician input, a first set of alternatively selectable prescribed applications relating to a diagnosis or treatment of the patient; displaying, on a user interface of a portable computing device of the patient, indicators of the prescribed applications of the first set; selecting, in response to input by the patient into the portable computing device of the patient, a selected prescribed application from among the first set. The system then receives the selected prescribed application with the portable computing device of the patient in response to the selecting by the patient and initiates communication, selectively between the portable computing device of the patient and a computing system of a medical service provider associated with the selected prescribed application, a plurality of health data elements associated with the patient.

In yet another aspect, the system may include a first portable computing device operable by a patient or an associated caretaker that includes a wireless communication module for transmitting to and receiving data from a medical service provider; and a processor of the first portable computing device having a computer readable medium having stored thereon. The processor is configured for displaying, on a graphical user interface of the first portable computing device, one or more indicators of one or more applications associated with a treatment of the patient, the one or more applications identified in response to a physician input; receiving an input, with the first portable computing device, to select an application from the one or more applications displayed on the graphical user interface; receiving the selected application with the first portable computing device; and outputting, to a medical service provider associated with the selected application, a plurality of health data elements associated with the patient. In some embodiments, the processor is further configured to determine the one or more applications from a set of applications, identified from the physician input, based on an insurance coverage of the patient. The processor may also be configured to display a co-pay and/or fee associated with each of the one or more applications displayed on the graphical user interface.

In some embodiments, the first portable computing device includes a first-party framework configured for displaying and selection of the one or more applications by the patient. A second portable computing device associated with the physician may be used for receiving an input to facilitate identification of a set of applications relating to treatment of the patient. The system may further be configured to determine the one or more applications from the set of applications identified from the physician input based on an attribute of the patient, applications and/or treatment, such as any of those described herein.

In another aspect, a system for treating and/or diagnosing a patient includes a first portable computing device operable by a patient or an associated caretaker, the first portable computing device including a wireless communication module for transmitting to and receiving data from a medical service provider; a processor of the first portable computing device having a computer readable medium having stored thereon computer executable instructions configured for: identifying, in response to a physician input, a first set of alternatively selectable prescribed applications relating to a diagnosis or treatment of the patient; displaying, on a user interface of a portable computing device of the patient, indicators of the prescribed applications of the first set; selecting, in response to input by the patient into the portable computing device of the patient, a selected prescribed application from among the first set; receiving the selected prescribed application with the portable computing device of the patient in response to the selecting by the patient; and initiating communication, selectively between the portable computing device of the patient and a computing system of a medical service provider associated with the selected prescribed application, and in response to the selecting by the patient, of a plurality of health data elements associated with the patient.

BRIEF DESCRIPTION OF THE DRAWINGS

FIG. 5 is a user interface of a portable electronic device of the patient illustrating a set of prescribed apps identified by the physician presented for selection by the patient in accordance with some embodiments.

DETAILED DESCRIPTION OF THE INVENTION

Figure 1:
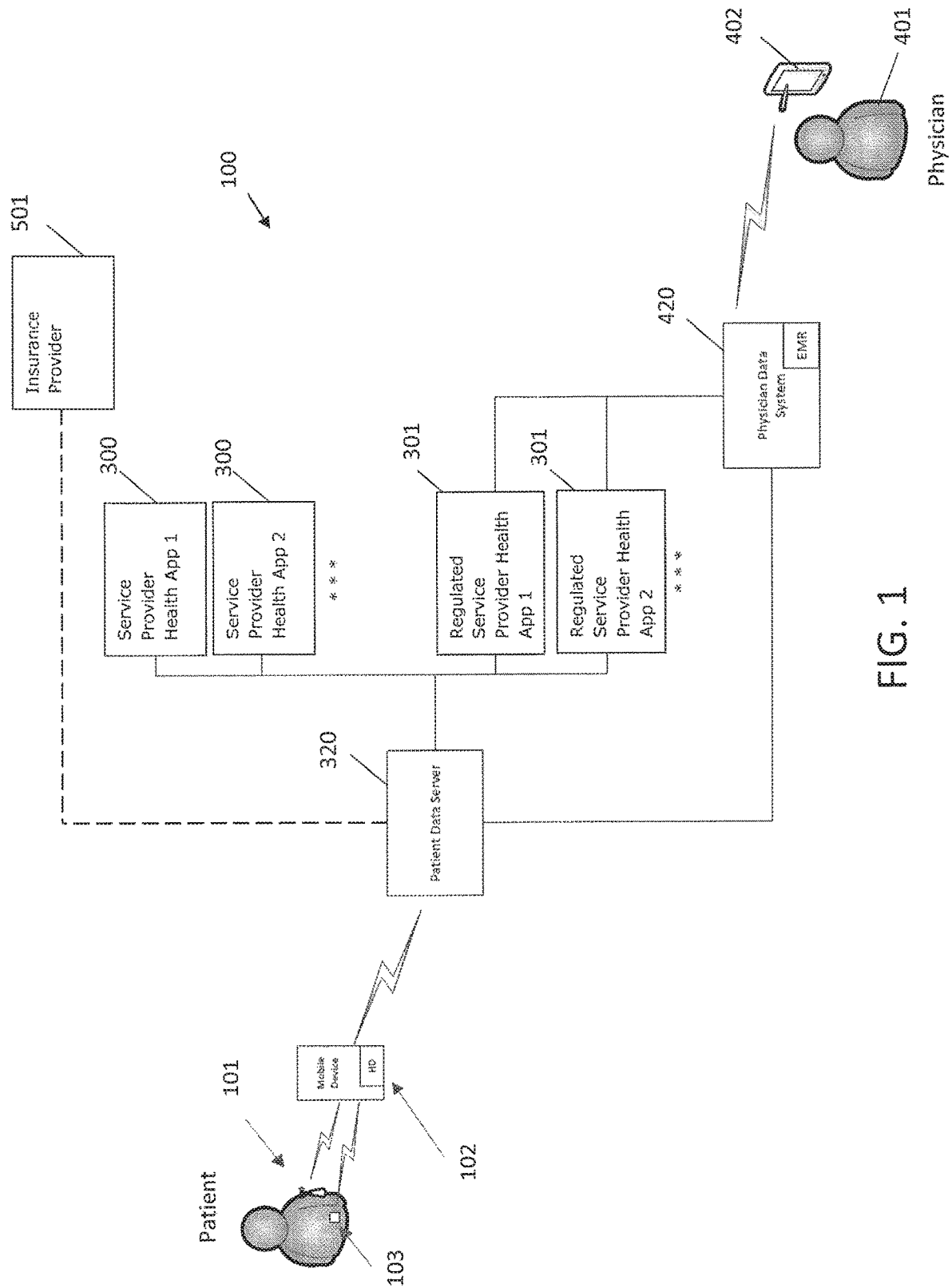
FIG. 1 is a simplified block diagram illustrating a system for identification of a set of health related applications prescribed by a physician and selection of the identified applications by the patient that may optionally be informed by insurance related information associated with the identified applications in accordance with embodiments of the present invention.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified so as not to obscure the example being described.

Embodiments of the present disclosure provide improved methods of treatment and diagnosis with enhanced identification of health related applications prescribed to a patient and selection of one or more identified health related application by the patient with a portable computing device. In some embodiments, the methods include improved communication of health related data accessible through the patient's personal computing device for use in the selected health related applications. In other embodiments, methods enhance selection of the one or more health related applications by displaying additional information regarding the application that relate to coverage or various other aspects on the portable computing device of the patient. Methods may further include communication of health information regarding the one or more health related applications between the portable computing device of the patient and the physician, health service provider, as well as the insurer or other health coverage entity. Such methods facilitate development of highly specialized health related applications and encourage competition between health related applications, thereby improving the functionality and ease of use associated with such health related applications. Such methods also streamline selection of benefits and reduce costs. In addition, such methods allow the patient enhanced autonomy in regard to the patient's personal experience in treatment and/or diagnosis. Such methods are advantageous in treatments and diagnostics that require a high level of daily or weekly interaction in tracking and/or monitoring various aspects of the patient with a health related application on the patient's portable computing device. This is especially useful in improving patient compliance since the needs and requirements of patients may differ widely from patient to patient, particularly between patients in different demographics (e.g., age, race, income level, gender) or geographical locations.

In one aspect, methods and systems of the invention facilitate identification of a set of health related applications by a physician for use in a treatment and/or diagnosis of the patient. In some embodiments, the physician selects one or more applications to prescribe to the patient, or one or more applications may be automatically identified by the same based on one or more factors associated with the treatment or diagnosis that are input by the physician, for example, a categorical selection, such as "heart disease," "diabetes," or "obesity." In some embodiments, the physician may select one or more additional factors associated with the treatment, diagnosis or patient that further refines the identified apps suitable for a given patient, for example, selection of gender, race, age or an insurance or health care plan of the patient. In some embodiments, the physician identifies the set of applications through a user interface on a portable computing device, laptop, desktop, or other computing device. The set of apps are identified by the system in response to the physician input into a physician computing system and are output to a computing device associated with the patient, typically a portable computing device of the patient such as a smartphone or tablet device.

In another aspect, the system includes a portable computing device of the patient and a data processing framework for downloading and using applications that provide access to functionality which is FDA regulated, or which is prescribed by a physician. The physician may "prescribe an app" by identifying a set of applications to provide a desired FDA regulated medical functionality. Alternatively, the physician may provide an input relating to the type of application, treatment and/or diagnosis and the system identifies a set of applications in response. This identification may be performed by the framework on a physician server, the patient device or an associated server. In some embodiments, the set of applications, as presented to the patient, may include a subset of the apps approved by an insurance provider of the patient and one or more additional attributes associated with each application. For example, the system may indicate a co-pay associated with that insurance provider for each application of the subset.

After identification of the set of applications, the system allows the user to select from among the set of applications and the selected application may communicate data from a regulated or non-regulated device of the patient to an FDA regulated service provider associated with the selected application. In some embodiments, there may also be clinical data (e.g. clinical data requests, diagnostic output data, therapeutic device instructions) exchanged between the selected service provider and the physician. Optionally, one form of output from the selected service provider may be sent to an electronic medical record maintained by the physician with the same or another form of data being sent to a repository of health related data from the portable computing device or an associated regulated device of the patient, such as sensor devices (e.g., blood glucose sensor, heart rate sensor and the like).

In another aspect, methods of the invention include: identifying a set of applications to provide a desired FDA regulated medical functionality as well as selecting a subset of apps based on an insurance provider of the patient or the like, and selecting one or more health related applications by the patient on a portable computing device from among the set of applications displayed on the portable computing device. In some embodiments, one form of data from the selected service provider may be sent to an electronic medical record maintained by the physician with the same or another form of data being sent to a repository of health data (e.g. database, server, cloud) accessible by the portable computing device or a regulated device of the patient. In some embodiments, financial data associated with the medical functionality performed by the service provider and/or the physician, optionally including medical fee-for service or reimbursement data, may also be exchanged between the service provider, insurance provider, physician, and/or patient.

In some embodiments, the system may be implemented as a computing device configured with a memory and a processor. The processor may be configured to execute instructions stored on the memory to configure the memory to identify whether health information data stored on the memory or accessed by the device is patient authorized data suitable for use with the selected health related application. In addition, the processor may be configured such that a subset of data, which is not patient authorized data, is excluded from the communication to the selected application and is not sent to the third-party service provider or physician, as well as excluded from the patient's electronic medical record. This aspect further safeguards patient privacy while providing the improved functionality associated with prescribed health related applications. According to another embodiment, a computer-readable medium may include instructions that, when executed, configure a computer processor to receive, from a service provider, instructions for implementing a background process configured to manage authorization and release of various types of data. The instructions may further configure the processor to receive, from the service provider, a data download that includes information about a new data type. The instructions may also configure the processor to receive, from an application, a request to access data corresponding to the data type, and provide, to the application, the data corresponding to the data requested based at least in part on interpreting the received data download.

Embodiments of the present disclosure are directed to, among other things, managing personal information received from external sources, or from other peripheral devices of a user. In some examples, the information collected by the data collection devices may be provided to a user device of the patient (e.g., a mobile phone, a tablet computer, a laptop computer, a wearable computing device, etc.) and/or one or more first-party or third-party applications of the user patient device, before being selectively transmitted to a physician for a treatment. In some examples, a first-party application may be one that is provided with the operating system (O/S) of the user device, is configured to operate natively with the user device, provided by the developers of the O/S for use with the user device, and/or trusted by the O/S and/or device. A third-party application may be one that is provided by a third-party or entity other than the developer/manufacturer of the user device and/or it's O/S. Examples of information being collected and/or managed may be health, fitness, and/or activity information of the user (e.g., blood glucose levels, weight, height, calories burned, heart rate, etc.). The user information may be categorized or otherwise identified by one or more data types (or categories). Weight, number of steps walked, number of calories burned, heart rate, etc., are each an example of such health data. Other data types (e.g., outside of health information) are also envisioned including, but not limited to, hours worked, hourly rate, miles per hour, pages read per minute. A user device of the physician allows for ready selection of a set of data of health information relevant to treatment and/or diagnosis, while the user device of the patient determines a subset of the requested data set authorized by the patient to be sent to the physician.

In some embodiments, a first-party application framework may be executed on a user device of the patient that is configured to receive, store, manage, and/or provide such user information to the service provider, to third-party applications, to other first-party applications, and/or to local storage of the user device. As part of the first-party framework, a first-party process may be executed by processors of the user device. The first-party process may include, but is not limited to, a daemon or other background process configured to communicate with the third-party applications, the O/S of the user device, and/or electronic storage of the user device. In some instances, first-party process may be configured to manage a data interchange for sharing some user data with third-party applications as well as the physician. In this way, the first-party process may allow the physician to access user information that was initially provided by the third-party application, a first-party application, or other third-party applications. Since health information of a user may be considered extremely personal and/or confidential, the user is provided with the ability to protect or otherwise not share some of the heath information with the physician, third-party service provider, or insurer. In some examples, each third-party application may be instructed to request authorization for accessing particular (or all) data from the data interchange before transmitting any processed health data to the physician.

In some embodiments, once installed, the third-party applications may be able to subscribe to certain data types, and the first-party process may be configured to automatically wake up the third-party application (e.g., in the background) and ensure that the third-party application is able to process the data as needed to transmit requested data to the physician. For example, a third-party application of the user may subscribe to a blood pressure data type and indicate an associated subscription frequency. Based at least in part on that frequency, when a new blood pressure reading is received by the first-party process, the process may wake up the appropriate third-party application background, provided with the new data and provide it with the updated data. The process may then wait for confirmation that the third-party application has processed the data. If the process does not receive the confirmation within a specified time, the process may again launch the third-party application, provide the data, and wait for confirmation. In this way, the process can ensure that the third-party application receives the data even if the user has not explicitly requested it. In this manner, the physician can receive the most recent up to date health information requested.

In some embodiments, a plug-in framework may be utilized to implement data types that are initially available for use by the first-party process and/or registered third-party applications. Plug-ins of the plug-in framework may register new data types that adhere to different identifiers so they can store their own data in the database automatically. In some examples, the plug-ins may be implemented as code that can read application programming interface (API) method calls with identifiers and/or strings associated with the data types. This may facilitate classification of types of health information to allow ready selection of requested data sets by the physician as well as allowing the patient ready authorization of data to be sent. Further, by utilizing an asset download, a service provider may enable the addition of new data types not initially provided with the first-party process (e.g., on demand). As such, the service provider may identify one or more data types not initially implemented within the first-party framework that are being requested by users/developers. The service provider may publish information about the new data type and/or how to utilize it, as well as identify whether the data type is authorized for release to a physician or medical facility upon request.

In other embodiments, the first-party process or framework or an associated first party application sets an authorization status of each field of data upon being received or accessed. The authorization status may be informed by a setting or input into the third-party application or may be set independently from the third party application. For example, a user patient may set or classify each item of information or type of data as a setting or selection made within the first-party framework of the patient device, regardless of any authorization setting made with a third-party application. This aspect facilitates improved control of patient authorizations for release of health information data to a physician, since the authorizations can be set and controlled by the patient from a central location using the first-party process itself. In another aspect, the first party process includes a prompt to the user requesting that the user set an authorization status of a field of information or type of information. This may be performed upon receipt of new information or types of information or before releasing of information after a request for the information has been made by the physician.

FIG. 1 illustrates a simplified diagram of a prescribed application system 100 in accordance with embodiments of the present invention. The system facilitates identification of a set of health related applications 300, 301 prescribed by a physician 401 to the patient and selection of one or more of the health related applications by the patient using a portable computing device 102. In some embodiments, the system informs selection of the health related application(s) by the patient by displaying additional information regarding each of the one or more health related applications, for example, information relating to health care coverage (e.g. co-pays, coverage, incentives). This additional information may be received directly from the insurance or health care coverage entity 501 or may be obtained indirectly through another source, such as through a database updated by health care providers or updated through a physician data system 420. The set of health related applications identified may include non-regulated health applications 300 as well as regulated health application 301. Examples of non-regulated health applications 300 may include applications that track/monitor/analyze information that is not generally regulated, such as a daily heart rate monitor, a range of movement, or steps per day. Examples of regulated health applications 301 include tracking, monitoring and/or analyzing information or use of devices that are generally FDA regulated, such as blood glucose measurement/tracking, blood pressure tracking, heart decompensation detection and the like. In one aspect, some health related applications may be available only by prescription.

The system 100 includes a portable electronic computing device 102 (e.g. smartphone, tablet) associated with the patient through which the patient or a caretaker of the patient (e.g. parent, nurse) can receive a communication from a physician data system 420 regarding health application prescriptions and select and install one or more of the prescribed health related applications for operation and use on the portable computing device 102. The system facilitates communication of the prescribed health related applications between a physician data system 420 and the portable computing device 102 of the patient. Identification of a set of prescribed health related applications is performed in response to an input received from the physician associated computing system 420, typically in response to an input from the physician 401, which may be input into a computing device, such as a portable computing device 402 (e.g. smartphone, tablet) of the physician 401. The physician input may be an individual selection of one or more health related applications 300, 301 or may be an input from which the system identifies a set of multiple health related application, for example, the physician input may be a categorical selection (e.g. heart condition, diabetes) from which a set of related health service applications are selected by the system. The selection of the health related application by the system may be informed by one or more additional factors relating to the physician, the patient, the portable computing device of the patient and/or the treatment or diagnostics for which the applications are prescribed. Factors relating to the physician may include aspects relating to the physician's specialty or associated medical facility. Factors relating to the portable computing device may include capabilities of the portable computing device (e.g. operating system). Factors relating to the patient may be any attribute of the patient, which may include aspects of health care coverage (e.g., insurance, co-pays, network of providers) or any personal or demographic information that may be associated with the patient.

Once the one or more health related application are selected by the patient, the one or more applications are installed on the portable computing device 102 of the patient for use in treatment and/or diagnostics. In one aspect, the portable computing device 102 of the patient includes a plurality of health data elements stored on a memory of the device or on a patient data server 320 (e.g. server, cloud) accessible to the first portable computing device 102. Health information of the patient is received in the mobile device 102, either input by the patient or acquired from one or more sensor devices, such as a wearable sensor device 101 or a specialized auxiliary sensor device 103, and wirelessly transmitted to the patient data server 320. The patient data server 320 may be coupled to any number of third-party service providers or the regulated medical service providers associated with the health related applications 300, 301 that may utilize the acquired health information received from the patient data server 320 and perform additional health related services, such as processing health data to determine trends or various other health metrics. Such processed data is generally made available to the mobile device 102 through the patient data server 320. The physician electronic device 402 is communicatively coupled with the physician data system 420, which includes access to the electronic medical record (EMR). The physician data system 420 may also be coupled to one or more regulated medical service providers 301 and the patient data server 320. In this system, the mobile device 102 of the patient and the physician device 402 are communicatively coupled through the patient server 320 and physician data system 420 such that the communication session can be conducted remotely without requiring the patient to visit the clinic and allow rapid transmission of targeted relevant data needed for the session, while also safeguarding patient privacy.

In one aspect, mobile devices 102 in combination with the one or more sensor devices, in this example, a wearable device 101 and/or auxiliary sensor device 103, that allows collection and/or analysis of large amounts of health data, typically far greater amounts than conventional medical visits entail. Dealing with such large amounts of data, however, may negate any associated benefits such information provides as it may prove difficult and overly time consuming to manage using conventional methods. The above described system provides a method of dealing with requesting of relevant data from vast amounts of data in a rapid and manageable manner and facilitate submission of the requested data to the physician while still safeguarding patient privacy, thereby improving efficiency and feasibility of using such large amounts of data in treatments and diagnostics. In addition, the manner in which each application interacts with the patient may differ considerably such that selection of the application by the patient can be crucial in maintaining patient compliance in using the prescribed health related application for the duration of treatment.

In some embodiments, the health information used by the selected health related applications 300, 301 may be input directly into the mobile device 102 by the patient or may be obtained through one or more health information acquisition devices or sensors, such as wearable devices 101 or specialized auxiliary sensor device 103. Wearable devices 101, such as a watch, wristband, or patch, include an associated sensor that measures one or more parameters that can be used to determine health data, either directly or indirectly, when worn by the patient. For example, the wearable device 101 may measure body temperature directly or may measure activity levels by use of one or more accelerators. In some embodiments, the wearable device 101 is incorporated within the first-party framework of the mobile device 102. The one or more auxiliary sensor devices 103 may be specialized for sensing and/or measuring various health metrics, including but not limited to activity level, activity tracking, respiration, body temperature, heart wellness data, hydration levels, perspiration, blood glucose, salinity, sleep cycles, posture, $O_2$ levels, muscle engagement, or any combination thereof. The collected data may or may not be specific to the condition being treated and/or diagnose and may be collected without requiring any additional input from the patient to initiate collection of the sensed data. In some embodiments, the sensed data is collected over a duration of time, the duration generally exceeding a few days, such one or more weeks, months or years. Typically, these auxiliary health sensor devices 103 are third-party devices that are supported by a third-party application and managed by used of a third-party service provider 300. Such sensors 103 may also be a regulated medical device that is supported through a regulated medical service provider 301. The mobile device 102 communicates the health information to the patient data server 320, which may be selectively accessed by the physician data system based on identification of a subset of data authorized by the patient to be released by the physician.

Figure 2:
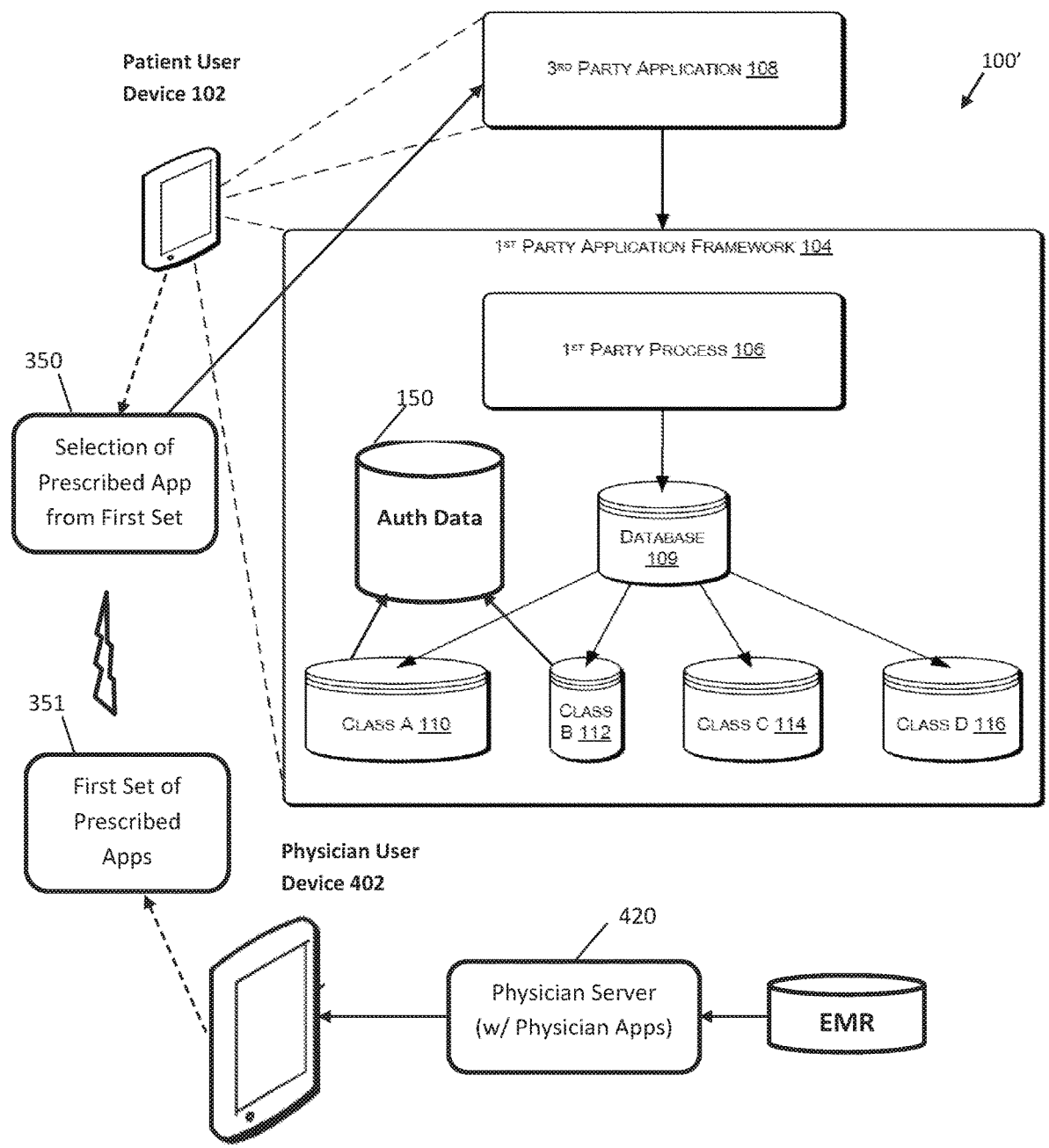
FIG. 2 is a simplified block diagram illustrating an example system architecture for managing user information in regard to the prescribed app selected by the patient in accordance with some embodiments.

FIG. 2 illustrates a simplified architecture diagram 100' depicting a patient device 102 configured to implement a selection and installation of a prescribed health related application with a first-party application framework 104 and managing exchange of health information (e.g., the plurality of health data elements) received by the mobile device 102 for use in the patient selected third-party health related application 108. As noted above, the first-party application framework 104 may be configured as an application framework for managing selection of prescribed applications by the patient and for managing user data of a plurality of data collection devices for use in the patient selected applications. While health data is used as an example throughout much of this disclosure, any type of data that may be collected or otherwise provided about a user may be managed by the first-party application framework 104. In some examples, because the first-party application framework 104 is provided or otherwise controlled by developers of the user device 102 and/or its associated O/S, the first-party application framework 104 may be considered a trusted framework with full access to all user data. In some examples, the first-party application framework 104 may be configured with one or more processes executed by the user device 102. For example, a first-party process 106 may be executed in the background such that the user is not aware that it is running. In this way, the first-party application framework 104 may be able to manage the user data whenever desired without interfering with the everyday use of the user device 102. Additionally, in this way, the first-party application framework 104 may be able to communicate with one or more third-party applications 108 to allow for rapid transmission of the health data to the physician, including processed health information from the selected application relating to the treatment or diagnosis for which the application is prescribed.

In some examples, the first-party process 106 may be configured to manage (e.g., store, retrieve, encrypt, etc.) user data via a database 109 of the user device 102. Such data may include various differing types of user data, including data relating to health care coverage (e.g. co-pays, networks of providers, incentives) that may be used by the frame-work when displaying the set of prescribed programs to the patient for selection. As part of the first-party application framework 104, the database 109 may be divided or otherwise logically separated into a plurality of classes of data stores. For example, the user data may be stored in at least one of a class A data store 110, a class B data store 112, a class C data store 114, and/or a class D data store. In some examples, the class A data store 110 may be configured to store personally identifiable user information (e.g., personal health, fitness, or activity data). In some examples, this data is only available to the third-party application 108 when the user device 102 is unlocked. By way of example, the user device 102 may be unlocked when the user associated with the user device 102 has correctly entered his or her user identifier (ID) and password (e.g., when logging in and/or unlocking the lock screen). Class B data store 112 may be configured to store "journal" type data. Journal data may include, but is not limited to, personally identifiable user information and/or other metrics associated with use of one or more data collection devices and/or the third-party application 108. When the user device 102 is locked, the journal data of the class B data store 112 may be inaccessible to the third-party application 108. However, in some examples, data from a data collection device or an application (e.g., the third-party application 108) may be read from or written to the class B data store 112 by the first-party process 106 while the device is locked as long as the first-party process 106 is active. If, however, the first-party process 106 fails or otherwise becomes inactive in the process of reading or writing data to the class B data store 112, the data may become permanently inaccessible, and new data may not be written to the class B data store 112 until the first-party process 106 and/or a new session of the third-party application 108 have relaunched. In this way, the data of the class B data store remains securely accessible because it is only accessible to the first-party process 106 while receiving data from a third-party application 108 during the active session, and no other applications can read that data.

In some aspects, the class C data store 114 may be configured to store metadata associated with the management of the user health, fitness, and/or activity data. This metadata, in some cases, may only be accessible after the first unlock of the user device 102. As such, if the user device 102 reboots (based at least in part on a software issue or a loss of battery power), this data may not be available until the user unlocks at least once. The metadata stored in the class C data store 114 may include subscription information, access permission information, and/or safe metadata, but may not, in some examples, identify or be directly associated with any health information (e.g., the data stored in the class A data store 110). The class D data store 116 may be configured to store free-form (e.g., unstructured) information provided by the user. In some examples, this may be health data; however, it may not be updatable and/or linked to any third-party applications (e.g., the third-party application 108) or data collection devices. The class D data may always be available to the first-party process 106 and/or the third-party application 108. In some aspects, the class D data may be pre-filled using information from the third-party application 108 and/or one or more other applications or processes. However, the user may be able to enter additional data, update the data, include incorrect data, or otherwise configure the information in the class D data store 116 as they see fit. The class D data may be available on the lock screen of the user device 102 without anyone (e.g., the user) logging in or otherwise unlocking the user device 102. In this way, the lock screen or another accessible screen of the user device 102 may be analogous to a medical ID bracelet. In some cases, an emergency icon or other function on the lock screen may enable the presentation or rendering of the class D data upon request for anyone (e.g., an emergency medical technician or the like) to see. Further, in some aspects, the third-party application 108 may not have access to the class D data, in part because it may be unstructured data that would be difficult for the third-party application 108 to process.

In one aspect, the first-party framework 104 identifies health information data authorized by the patient for use by the selected prescribed application as Authorized Data 150. Such an identification may be based on a default, a pre-selection or a live input from the patient in response to a query. Typically, the most common types of information being requested and identified as Authorized Data would be Class A and Class B types of information. Some embodiments may include release of various other types of data, for example to allow further processing of collected data by the selected application on the physician device. While Authorized Data 150 is shown schematically as a separate element, it is appreciated that such authorized data is not required to be stored in a separate location, nor is it required to be identified before the request for information is made. This may instead be accomplished in various different ways, for example, by tagging or using a specific identifier for each field of data to denote which data items are authorized for release by the patient and to which parties the data is authorized for release. In some embodiments, the identification of authorized data is determined only after receiving a request for data. In systems having exceedingly large amounts of health information data, this approach may be more efficient, since the data is only analyzed to determine authorization of the data set that is being requested. Since a physician has limited time and resources to review health information for each patient, the amount of health information would generally be limited and targeted to factors most relevant for that patient and/or the condition being treated or diagnosed. Typically, once authorization and permissions are set by the patient, or once the default authorizations or permissions are accepted, no further authorization or permissions are needed during subsequent use of the selected prescribed applications to allow the selected prescribed application to access the authorized patient data and/or to communicate the authorized health data or processed derivate data to the physician for use in treatment and/or diagnosis.

As shown in FIG. 2, communication of the set of prescribed applications from the physician to the patient may be facilitated by use of an application common to both a patient device 102 and a physician device 401. Such devices may communicate through a common server (e.g., physical server or cloud) that supports the common application, as opposed to going through separate but interconnected server information. The physician device may separately couple with the physician server 420 as well as the electronic medical record to import additional information external to the health information data associated with the mobile patient device 102 for use in identifying the set of prescribed applications for selection by the patient. Identifying the set of prescribed applications may be accomplished by one or more tasks performed by a computing system in communication with the portable device of the patient and/or performed by the portable device of the patient. While the application may be common to both devices, generally, the application would include features suited for the particular uses associated with each device. In addition, the application of the patient device requires a feature that allows the patient to select the prescribed application as well as any data authorizations for use in the selected application, while the physician device application requires a feature that allows the physician to select prescribed applications either individually, or allow automatic identification by selecting various options or inputting data relating to the patient (e.g. patient attributes, type of treatment or diagnosis). In some embodiments, this application is a first-party application on each of the devices and may be incorporated partly or fully into the first-party framework. For example, the application may run in the background during normal operation of either device, so as to be readily responsive to a communication from either device using the application. By using a first-party application or platform for facilitating session communication regarding prescribing of applications, selection by the patient and subsequent operation of the selected application, the system allows a central location from which the patient can manage the selected health related applications and authorize release of data that may be provided to various entities (e.g. third-party application, third-party servers, physician). While these different entities may each include their own permission and authorizations regarding storage and transmittal of secure health information data, routing the transfer of data through the first-party application ensures that the patient is aware exactly what data is being released and allows the patient an opportunity to change authorizations of data and release data, regardless of permissions associated with the third-party application or other data source.

In some embodiments, one or more third party applications may be in communication with the first-party application framework 104 and/or the first-party process 106 for providing user information collected by a health data collection device 103. In some examples, the data collection device 103 may be any wearable or specialized mobile device configured to collect activity, health, medical, and/or fitness information about a user. This information may then be provided to one of the third-party applications via one or more networks. Once received by the third-party source application 303, the information can be provided to the first-party process 106 for storage in the database 109.

Figure 3:
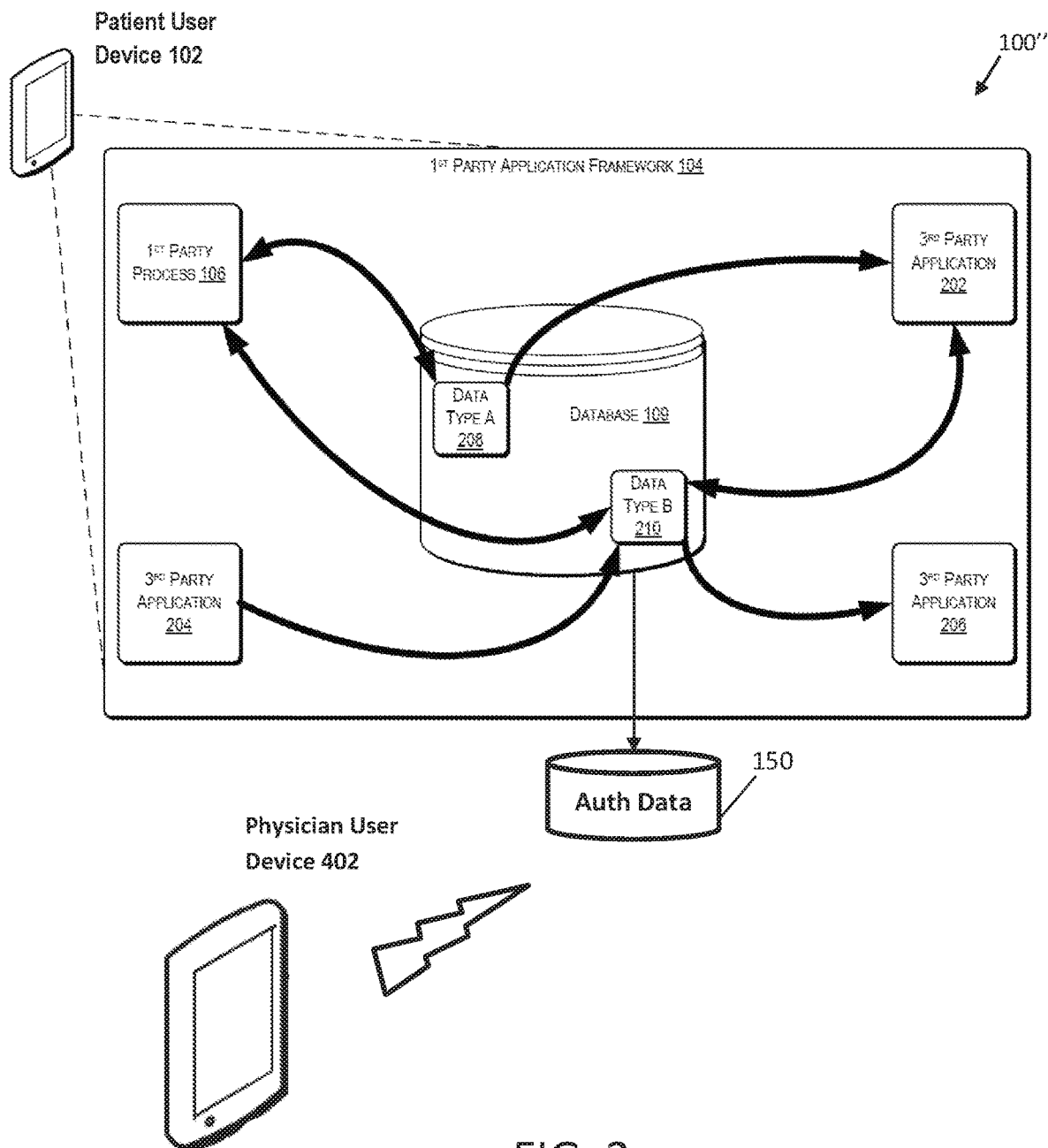
FIG. 3 is another simplified block diagram illustrating another example architecture for managing user information in regard to the prescribed app selected by the patient in accordance with some embodiments.

FIG. 3 illustrates a simplified architecture diagram associated with another system 100" that depicts additional implementation details associated with the first-party application framework 104 and how user data stored in the database 109 can be accessed by the first-party process 106 and/or utilized by one or more different third-party applications 300, 301 selected by the patient. In some examples, as noted above, the database 109 may allow the first-party process 106 and/or the third-party applications 300, 301 to write health and medical data, including data from sensor device 101, 103 into the database 109 and read it back out. In various aspects, the third-party applications 300, 301 may actually populate the database 109 with data more than the first-party process 106. Thus, the first-party application framework 104 may be configured to act as a data interchange between the applications as well as to the physician. In some aspects, the type of data available to the selected applications may differ according to the type of application selected. For example, a non-regulated application 300 (e.g. heart monitor) may have access only to limited types of data (e.g., Data Type B), which may include heart rate information from a wearable sensor in communication with the portable device, while a regulated application 301 may have access to additional types of data (e.g., Data Type A) as needed for its particular function.

In some embodiments, the portable device of the patient or an associated framework is configured to identify whether health data stored on or accessible with the device is authorized to release for use with the selected application, the third-party health a health service provider, and/or the physician. Such identification may made upon receiving or storing of the data, or may be made at later time, such as after receiving a request for a set of health data that includes the given data. The identification may be broadly applied to all health care providers, or may be adapted for a class of providers or for a given application. For example, one such item of information that a user may desire not be included in released health information is an activity level. An activity level may be a metric provided by a first party process or application or a third party application. The patient user may set the activity level as private such that it is available only to the associated first party process/application or third party application.

As noted above, the user device 102 may be configured to manage a data interchange for reading and/or writing user data to the database 109, and for sharing that user data among one or more authorized third-party applications. In some examples, the data collection device 302 may be configured to provide health, fitness, activity, and/or medical data of the user to a third- or first-party application (or process). In turn, this data may be shared, aggregated, and/or accessed via the first-party framework module 104 that may be configured to implement the first-party application framework 104 of FIGS. 2-3. The user device 102 may be any type of computing device such as, but not limited to, a mobile phone, a smartphone, a personal digital assistant (PDA), a personal computer (e.g., laptop or desktop), a thin-client device, a tablet computer, an electronic book (e-book) reader, a wearable device, etc. In some examples, the patient device 102 may be in communication with the service provider computers 304 and/or the data collection device via the networks shown or via other network connections.

In one illustrative configuration, the user device 102 may include at least one memory and one or more processing units (or processor(s)). The processor(s) may be implemented as appropriate in hardware, software (e.g., computer-executable instructions, firmware, etc.), or combinations thereof. Computer-executable instruction or firmware implementations of the processor(s) may include machine-executable instructions written in any suitable programming language to perform the various functions described. The user device 102 may also include geo-location devices (e.g., a global positioning system (GPS) device or the like) for providing and/or recording geographic location information associated with the user device 102. The memory may store program instructions that are loadable and executable on the processor(s), as well as data generated during the execution of these programs. Depending on the configuration and type of user device 102, the memory may be volatile (e.g., random access memory (RAM)) and/or non-volatile (e.g., read-only memory (ROM), flash memory, and the like). The user device 102 may also include additional removable storage and/or non-removable storage including, but not limited to, magnetic storage, optical disks, and the like. The disk drives and their associated non-transitory computer-readable media may provide non-volatile storage of computer-readable instructions, program modules, data structures, and other data for the computing devices. In some implementations, the memory may include multiple different types of memory, such as RAM, static random access memory (SRAM), dynamic random access memory (DRAM), or ROM. While the volatile memory described herein may be referred to as RAM, any volatile memory (e.g., that does not maintain data stored therein once unplugged from a host and/or power) would be appropriate.

Additional types of computer storage media that may be present in the user device 102 may include, but are not limited to, phase-change RAM (PRAM), SRAM, electrically erasable programmable read-only memory (EEPROM), flash memory, compact disc read-only memory (CD-ROM), digital video disc (DVD), magnetic cassettes or tape, magnetic disk storage, or any other medium that can be used to store the desired information and that can be accessed by the user device 102. Combinations of any of the above should also be included within the scope of non-transitory computer-readable media. Alternatively, computer-readable communication media may include computer-readable instructions, program modules, or other data transmitted within a data signal, such as a carrier wave, or other transmission. However, as used herein, computer-readable storage media does not include computer-readable communication media. The user device 102 may also contain communications connection(s) that allow the user device 102 to communicate with a data store (e.g., the database 109), or another computing device via one or more networks. The user device 102 may also include I/O device (s), such as a keyboard, a mouse, a pen, a voice input device, a touch input device, a display, speakers, etc.

Turning to the contents of the memory in more detail, the memory may include an operating system and/or one or more application programs or services for implementing the features disclosed herein including an authorization module 334, a background module, an extension module, and/or an aggregation module 340. In some examples, the authorization module may be configured to manage authorization requests from third-party applications for access of user data stored in the database 109. The authorization module may also be configured to mask when a user denies authorization to a third-party application for a particular data type. In this way, the third-party application may not be able to infer anything about the user based at least in part on the denial. The background module 336 may be configured to launch and/or relaunch third-party applications in as background process. In some examples, the background module 336 may also be configured to verify that the third-party application has finished processing the data it requested, by continuing to relaunch the third-party application in the background until notification is received that the third-party application has completed processing. The extension module 338 may be configured to handle registering new data types with the first-party framework module in order to extend the functionality of the first-party application framework 104 of the systems shown in FIG. 2 or FIG. 3. Further, the aggregation module may be configured to aggregate or otherwise combine (and, in some examples, provide presentation for) user data received from multiple different data sources. The service provider computers may also be any type of computing device such as, but not limited to, a mobile phone, a smartphone, a PDA, a personal computer, a thin-client device, a tablet computer, an e-book reader, a wearable device, and the like. In some examples, the service provider computers 304 may be in communication with the user device 102 and/or the data collection device 302 via one or more networks or via other network connections.

In some embodiments, including those shown in FIGS. 2 and 3, the patient user device 102 and physician user device 402 communicate directly with each other, such as through near field communication. It is appreciated that at least some of the information transmitted by either device may be accessed by the respective device through one or more networks associated with the device, or first-party applications or third-party applications. In some embodiments, the devices communicate with each other through an NFC module integrated within each device, using short-range RF module technology to transmit the identified health related applications and/or health information associated with the selected application. The entire process may be performed while the patient and physician are in close proximity, such as in an examination room of a clinic. Such systems illustrate the above noted advantages in efficiency over conventional methods by utilizing the same methods described herein even when the physician and patient are in close proximity.

Figure 4:
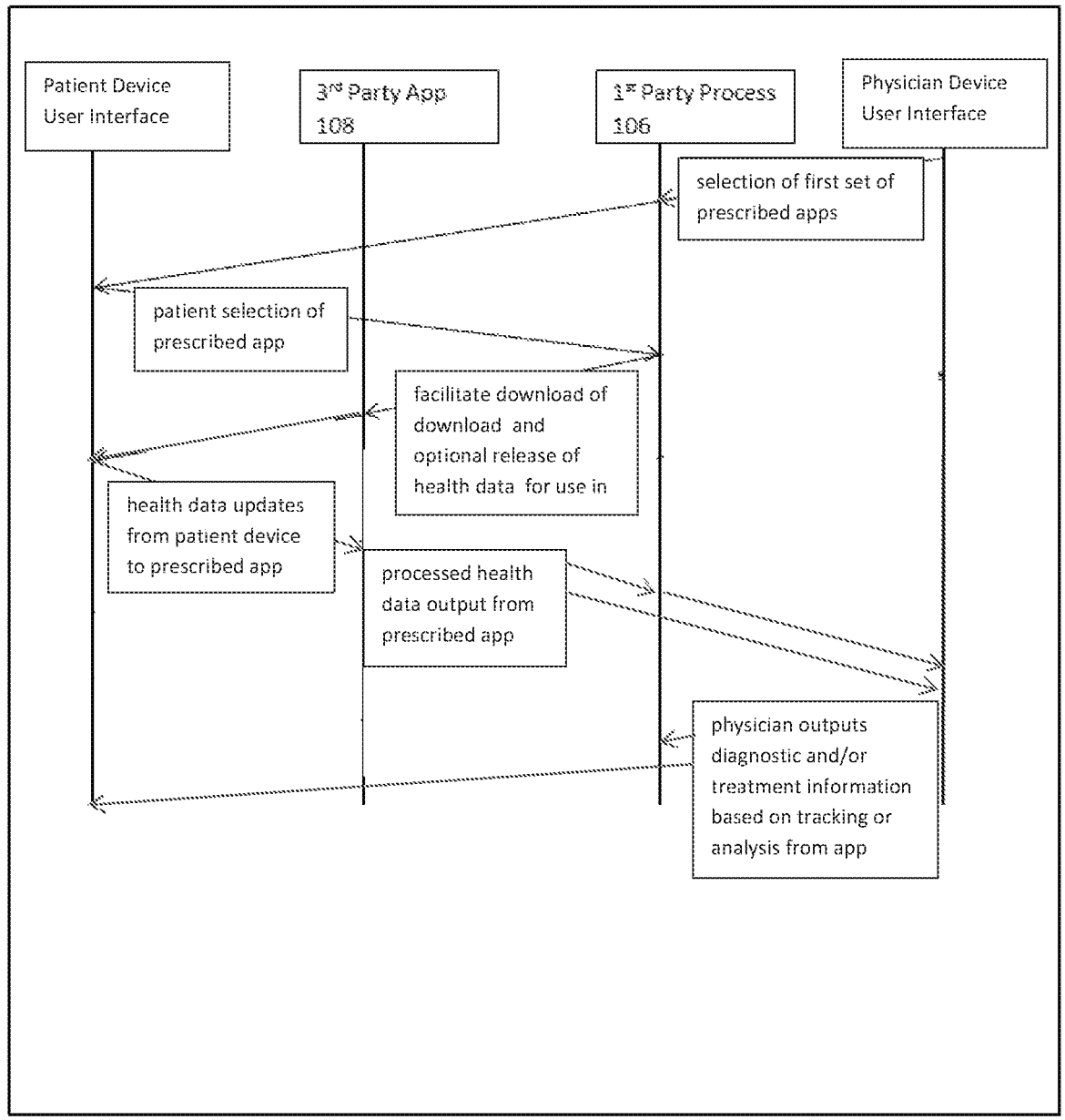
FIG. 4 is a sequence diagram steps associated with an example method of treatment utilizing identification and selection of prescribed apps with portable computing devices in accordance with some embodiments.

FIG. 4 illustrates an example sequence diagram describing features of the management of health information during a prescribed application communication session conducted using a system in accordance with the invention. After a visit to the physician by the patient or a tele-medicine session, a physician input initiates the process by which one or more health-related applications are prescribed. The physician may provide the input on a user interface of a physician device, such as a laptop or portable computing device. The system receives the physician input and identifies a first set of health-related applications that fulfill the requirements for the prescribed applications. This identification may be performed in a $1^{st}$ party process 106, which may operate on a portable computing device of the patient, a computing device of the physician or associated servers. After identification of the first set of applications, the first set of applications are presented to the patient on a user interface display of the patient device. Typically, the display includes a list of indicators, each indicator representing an application, along with one or more associated attributes (see for example FIG. 5). The patient then selects one or more of the health related applications for installation and use on the portable computing device of the patient. A first-party process may be used to facilitate download and installation of the selected health related applications and may also facilitate access or release of health data accessed by the portable computing device for use with the selected applications. Such health data may be stored on the phone or may include sensor data from one or more external or wearable sensors that is collected by the portable computing device. Once access is established, the portable computing device may periodically send updates of the health data to the health related applications or to the third-party health service providers and associated servers. The health related application may provide processed data (e.g. tracking, analysis) of the health data accessed by the application to the physician either directly, such as from a third-party server associated with the application, or may provide the processed health data to the physician through a first-party process associated with the portable computing device. The latter may provide additional controls regarding release of health data and provide additional protections to ensure that proper permissions and authorization is obtained before release of processed health data to the physician. Based on this processed health data, the physician may output diagnostic and/or treatment information to the patient through the portable computing device, such as in a tele-medicine session.

FIG. 5 illustrates an example display on a user interface of the portable computing device of the patient demonstrating how a patient can select one or more health related applications from a set of health related applications prescribed by the physician. Typically, the set of applications are presented to the patient as a list of identifiers 512-520 with the application names 502 as well as additional attributes that a patient may consider when selecting the application. These additional attributes may include but are not limited to the application service provider name 504 as well as health insurance or health care coverage information, such as the copay amount 506, whether the cost is reimbursable 508, whether the application is within a network of coverage 510, and any incentives 511 for using the application (e.g., reduction in monthly fees). It is appreciated that this display is but one example and that the set of health-related applications may include less or more information or features, as needed, in order to assist the patient in selecting the most suitable application.

Figure 6:
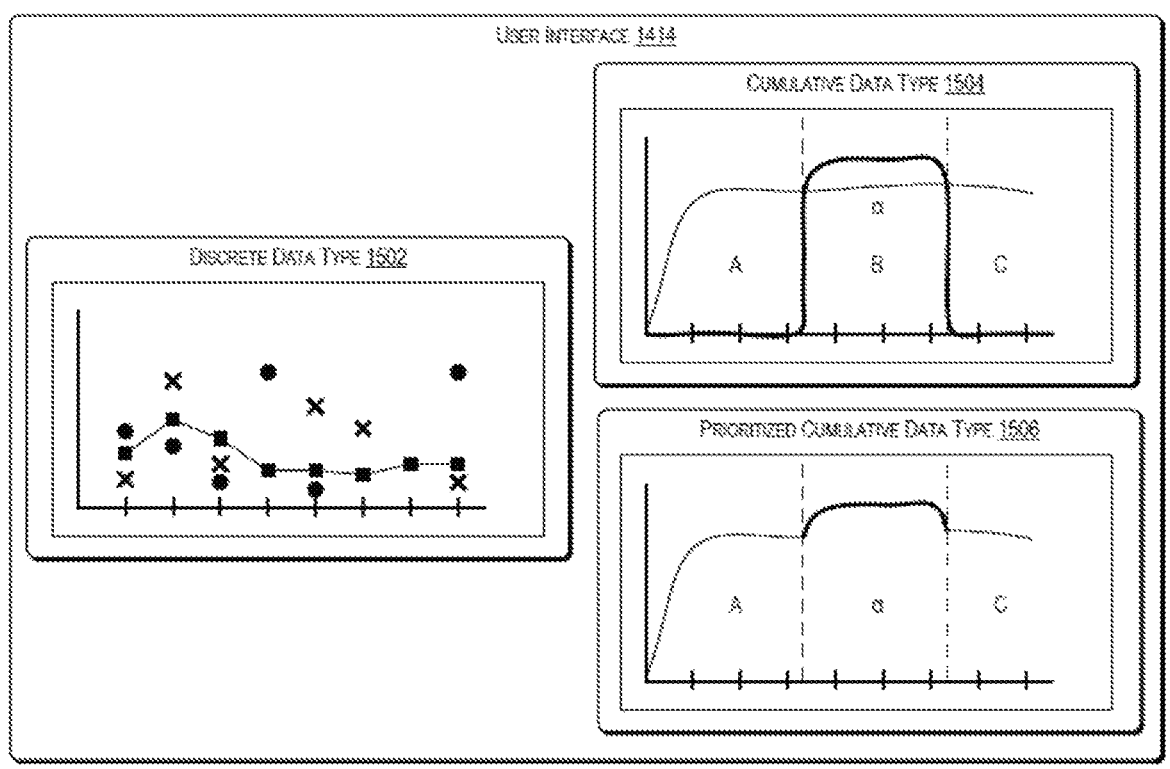
FIG. 6 is an example of tracking and/or analysis data provided by a prescribed health related app for output to a physician in accordance with some embodiments.

FIG. 6 illustrates an user interface 1414 illustrating different examples of different types of processed health data provided by health related applications. For example, for discrete data type presentations 1502, the UI 1414 may be configured to represent each data entry as a data point on a time graph. As shown, for the discrete data type presentation 1502, there may be multiple data entries for each segment of the total time period. For example, a user may have three different devices collecting their weight over the course of a day, week, month, etc. At each segment, the discrete data type presentation 1502 may include each data entry received by the first-party process 106 from the three different sources. Since weight is not a data type that would be added up over time (e.g., it is discrete), it may be appropriate to present each different data point for each segment. In some examples, a prioritized source may be identified by a line or other interface object/element that highlights the data points from that source. Here, the line connecting the square points on the presentation 1502 is one example of a way to represent priority or a preferred data source. These processed health data outputs may be displayed to the patient on the portable computing device or may be sent to the physician or associated server for use in treatment and/or diagnosis of the patient.

In some embodiments, when the health data acquired is cumulative, the data may be summed or otherwise added up over the entire time period. As shown in the cumulative data type presentation 1504, this may cause a double counting problem when multiple sources provide data for the same time segments. For example, over the first third of the time period, the first-party process 106 may only have received data from a first source (e.g., A number of steps). For a cumulative data type (e.g., steps walked), the data entries at each segment may be added together to get a total. Similarly, at the last third of the time period, the first-party process 106 may also have only received data from the first source (e.g., C number of steps). However, if two sources provided step data during the middle third of the time period, adding both B number of steps and alpha number of steps would not provide an accurate total step count because the number of steps during that time period would be double counted or at least counted from two different sources. As such, using the priority information collected from the user, the UI 1414 may be able to present a piecemeal representation such as the prioritized cumulative data type presentation 1506. In this presentation 1506, the alpha number of steps may have been identified as the user's prioritized data source for this subset of the time period. As such, only alpha number of steps (e.g., coming from one source) is shown during that subset of the time period, while A and C number of steps (e.g., coming from a different source). The total number of steps aggregated over the time period in this presentation 1506 may be A+alpha+C, as opposed to A+B+alpha+C from the cumulative data type presentation 1504. In some systems, the physician may desire particular types of data or processed data, such discrete, cumulative, or prioritized cumulative, or averaged data. Depending on what applications are provided on the patient device 102, the patient device may transmit processed data in response to a health information request from the physician.

Figure 7:
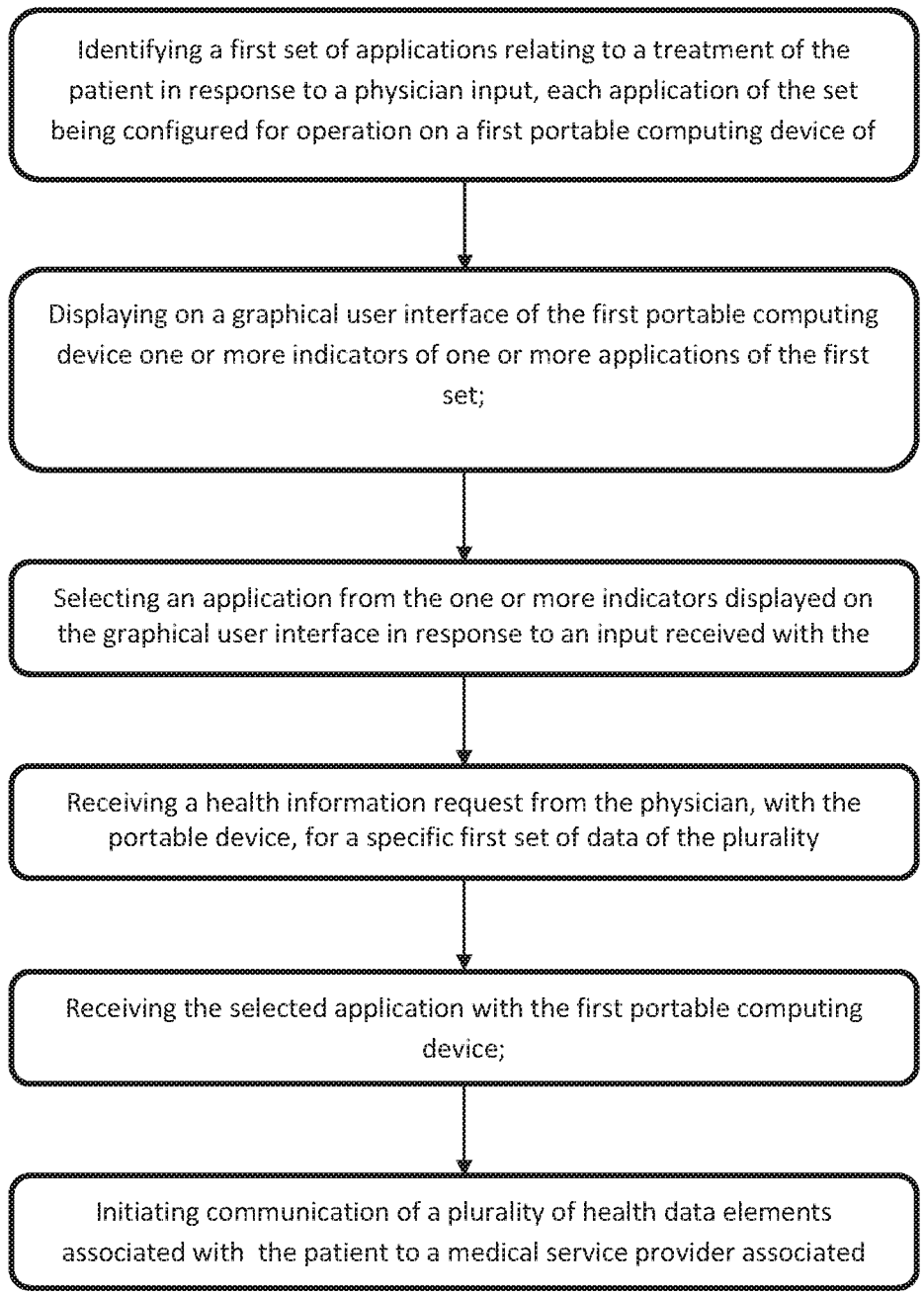
FIG. 7-9 are flow diagrams of example methods in accordance with embodiments of the invention.
Figure 8:
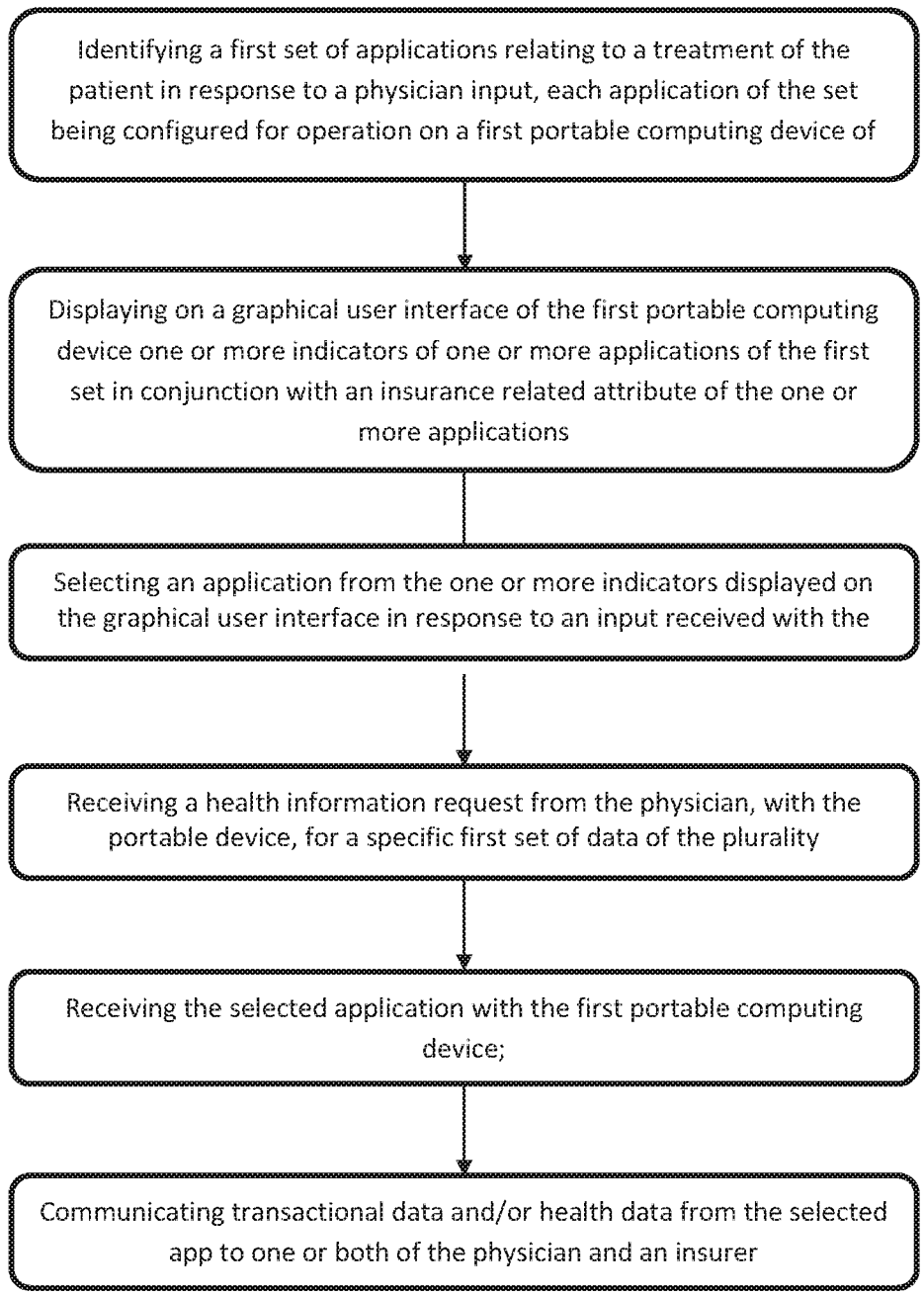
Figure 9:
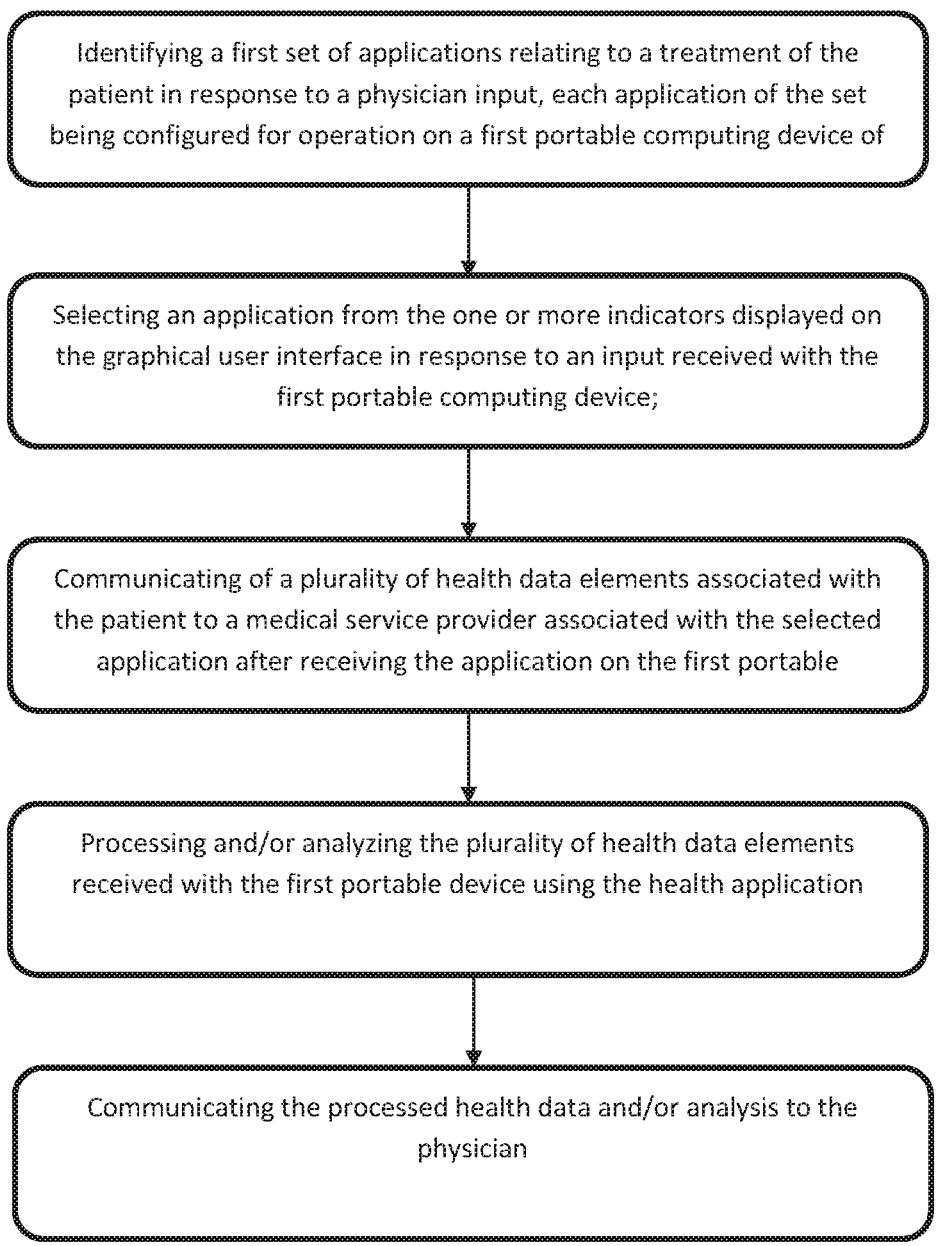

FIGS. 7-9 illustrate example flow diagrams showing methods by which prescribed health related applications can be identified and selected by the patient for operation on a portable computing device for used in treatment and/or diagnosis of the patient. The method of FIG. 7 includes steps of: identifying a first set of applications relating to a treatment of the patient in response to a physician input, each application of the set being configured for operation on a first portable computing device of the patient; displaying on a graphical user interface of the first portable computing device one or more indicators of one or more applications of the first set; selecting an application from the one or more indicators displayed on the graphical user interface in response to an input received with the first portable computing device; receiving a health information request from the physician, with the portable device, for a specific first set of data of the plurality receiving the selected application with the first portable computing device; initiating communication of a plurality of health data elements associated with the patient to a medical service provider associated with the selected application after receiving the application on the first portable computing device.

The method of FIG. 8 includes steps of: identifying a first set of applications relating to a treatment of the patient in response to a physician input, each application of the set being configured for operation on a first portable computing device of the patient; displaying on a graphical user interface of the first portable computing device one or more indicators of one or more applications of the first set in conjunction with an insurance related attribute of the one or more applications selecting an application from the one or more indicators displayed on the graphical user interface in response to an input received with the first portable computing device; receiving a health information request from the physician, with the portable device, for a specific first set of data of the plurality receiving the selected application with the first portable computing device; and communicating transactional data and/or health data from the selected app to one or both of the physician and an insurer.

The method of FIG. 9 includes steps of: identifying a first set of applications relating to a treatment of the patient in response to a physician input, each application of the set being configured for operation on a first portable computing device of the patient; selecting an application from the one or more indicators displayed on the graphical user interface in response to an input received with the first portable computing device; communicating of a plurality of health data elements associated with the patient to a medical service provider associated with the selected application after receiving the application on the first portable computing device; processing and/or analyzing the plurality of health data elements received with the first portable device using the health application; and communicating the processed health data and/or analysis to the physician.

Illustrative methods and systems for managing user device connections are described above. Some or all of these systems and methods may, but need not, be implemented at least partially by architectures such as those shown at least in FIGS. 1-9 above. While many of the embodiments are described above with reference to personal and/or health-related information, it should be understood any type of user information or non-user information may be managed using these techniques. Further, in the foregoing description, various non-limiting examples were described. For purposes of explanation, specific configurations and details are set forth in order to provide a thorough understanding of the examples. It is appreciated that the above examples may be practiced without certain specific details and that well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User devices (e.g., client devices) can include any type of general purpose personal computer such as, but not limited to, desktop or laptop computers running a standard operating system, as well as cellular, wireless, and/or handheld devices running mobile software and capable of supporting a number of networking and messaging protocols. These devices can also include other electronic devices, such as dummy terminals, thin-clients, gaming systems, or other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

The environment can include a variety of data stores and other memory and storage media as discussed above. These can reside in a variety of locations, such as on a storage medium local to (and/or resident in) one or more of the computers. Alternatively, the memory can be remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as desired.

The system and various devices may also include one or more software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

What is claimed is:

1. A method of treating a patient, the method comprising:
   executing an application framework by a first portable computing device of the patient, wherein the application framework is stored and executed on a memory of the first portable computing device, the application framework being specific for health diagnostics and/or treatment by prescribed health related applications;
   receiving a physician input, from a physician computing system, prescribing diagnosis and/or treatment of a given condition by a health related application, wherein the input includes a categorical selection of the health condition;
   identifying, automatically with the first portable computing device of the patient via the application framework by instructions recorded on the memory of the first portable computing device, a first set of a plurality of differing prescribed health related applications relating to a treatment or diagnosis of the patient for diagnosis or treatment of the selected health condition based on the physician input, each application of the first set being configured for operation on the first portable computing device of the patient;
   establishing, by the application framework, authorization and/or permission to access one or more applications of the first set by the application framework;
   displaying on a graphical user interface of the first portable computing device one or more indicators of one or more applications of the first set through the application framework;
   selecting a prescribed application from the one or more indicators displayed on the graphical user interface in response to an input received with the first portable computing device through the application framework;
   receiving, via the application framework, the selected prescribed application with the first portable computing device;
   receiving a plurality of health data elements associated with the patient over a duration of time from an output of one or more sensors external to the first portable computing device and associated with the first portable computing device and storing the plurality of health data elements on the first portable computing device;
   determining, with the application framework via instructions recorded on the memory of the first portable computing device, that a first set of the plurality of health data elements stored on the device is authorized to be released to the prescribed app;
   initiating, with the application framework, communication of the first set of the plurality of health data elements associated with the patient to the selected prescribed application; and
   outputting, via the application framework, processed health data generated by the selected prescribed application from the first set of the plurality of health data elements to the physician or health care provider.

2. The method of claim 1, wherein the first set of applications comprising alternatively selectable prescribed applications identified using a physician computing system in response to a physician prescribing any of the first set of applications, and further comprising receiving, with the first portable computing device of the patient, data identifying the first set of applications from the physician computing system.

3. The method of claim 1, wherein the first set of applications are a subset of applications identified based on an attribute of the patient or treatment.

4. The method of claim 3, wherein the attribute comprises any of: an insurance coverage of the patient, an age, a gender, a race, a demographic, a geographical location, and type of treatment.

5. The method of claim 1, wherein displaying the one or more indicators of the one or more applications includes displaying additional information including any of a co-pay, a cost, a third-party service provider name or affiliation, a reimbursement status, and an incentive associated with each of the one or more applications.

6. The method of claim 1, wherein identifying the first set of applications is based on a network of covered medical service providers associated with the physician.

7. The method of claim 6, wherein the first set of applications includes one or more applications by FDA regulated service providers.

8. The method of claim 1, wherein the plurality of health data elements communicated to the medical service provider comprises any of: a user input entered by the user on the graphical user interface of the first portable computing device, an output of one or more sensors associated with the first portable computing device, an electronic medical record maintained by the physician, or any combination thereof.

9. The method of claim 1, wherein the one or more sensors includes one or both of a wearable sensor and a specialized auxiliary sensor, each in communication with the first portable computing device.

10. The method of claim 9, wherein the one or more sensor devices detect any of: activity level, activity tracking, respiration, body temperature, heart wellness data, hydration levels, perspiration, blood glucose, salinity, sleep cycles, posture, $O_2$ levels, muscle engagement, or any combination thereof.

11. The method of claim 9, wherein at least one of the one or more sensor devices is an FDA regulated device.

12. The method of claim 9, wherein the one or more sensor devices comprises a cardiac sensor or an activity level sensor for treatment of a cardiac condition.

13. The method of claim 9, wherein the one or more sensor devices comprises an $O_2$ level sensor for treatment of chronic lung disease.

14. The method of claim 9, wherein the one or more sensor devices comprises a blood glucose meter for treatment of diabetes.

15. The method of claim 9, wherein the one or more sensor devices are configured to automatically communicate sensor data to the first portable computing device over the duration of time.

16. The method of claim 1, further comprising:
communicating a health data analysis output that is processed by the selected application to the physician.

17. The method of claim 16, further comprising:
receiving, with the first portable computing device through the application framework, an instruction from the physician regarding the treatment, the instruction being based on the communication of the health data analysis output.

18. The method of claim 1, wherein the first portable computing device comprises a first-party application framework through which the one or more applications are displayed to the patient and selected with the first portable computing device.

19. The method of claim 1, wherein the first set of differing applications comprise alternatively selectable prescribed applications relating to a diagnosis or treatment of the patient, wherein the first set of differing application includes some health related application available only by prescription.

20. The method of claim 1, further comprising:
after access is established, the application framework periodically sends updates of the first set of health data to the prescribed application.

21. A method of treating a patient, the method comprising:
executing an application framework by a first portable computing device of the patient, wherein the application framework stored and executed on a memory of the portable computing device of the patient, the application framework being specific for health diagnostics and/or treatment by prescribed health related applications;
communicating, via the application framework, one or more patient attributes stored on the first portable computing device to the physician or health care provider;
receiving a prescription input, from a physician or health provider computing system, prescribing diagnosis and/or treatment of a given condition by prescribed health related applications, wherein the input includes a categorical selection of the health condition;
identifying, via the application framework by instructions recorded on a memory of the first portable computing device, a first set of prescribed health related application for diagnosis and/or treatment of the selected health condition based on the prescription input and the one or more patient attributes;
displaying on a graphical user interface of the first portable computing device, via the application framework, a plurality of indicators of the first set of prescribed health related application, each indicator representing an application of the first set of prescribed health related applications;
selecting a prescribed application, via the application framework, in response to an input received with the first portable computing device of an indicator of the plurality of indicators;
receiving, via the application framework, the selected prescribed application with the first portable computing device;
receiving a plurality of health data elements associated with the patient over a duration of time from an output of one or more sensors external to the first portable computing device and associated with the first portable computing device and storing the plurality of health data elements on the first portable computing device;
determining, with the application framework via instructions recorded on the memory of the first portable computing device, that a first set of the plurality of health data elements stored on the device is authorized to be released to the prescribed app; and
initiating, with the application framework, communication of the first set of the plurality of health data elements associated with the patient to the selected prescribed application.

* * * * *